(12) United States Patent
Kaneko et al.

(10) Patent No.: US 6,517,523 B1
(45) Date of Patent: Feb. 11, 2003

(54) NEEDLE FOR INJECTION SYRINGE AND METHOD FOR MANUFACTURING THE SAME

(75) Inventors: Yukio Kaneko, Tochigi (JP); Takeyoshi Sakashita, Tochigi (JP)

(73) Assignee: Kaneko Kogyo Inc. (JP)

( * ) Notice: Subject to any disclaimer, the term of this patent is extended or adjusted under 35 U.S.C. 154(b) by 0 days.

(21) Appl. No.: 09/525,870

(22) Filed: Mar. 14, 2000

(30) Foreign Application Priority Data

Mar. 15, 1999  (JP) .......................................... 11-068654

(51) Int. Cl.$^7$ ................................................ A61M 5/32
(52) U.S. Cl. .............................. 604/272; 604/264; 163/5
(58) Field of Search ................................ 604/272, 273, 604/274, 264; 163/5

(56) References Cited

U.S. PATENT DOCUMENTS

| | | | | |
|---|---|---|---|---|
| 2,409,979 A | * | 10/1946 | Huber ......................... | 604/272 |
| 2,560,162 A | * | 7/1951 | Ferguson ..................... | 604/272 |
| 3,071,135 A | * | 1/1963 | Baldwin et al. ............. | 604/272 |
| 3,308,822 A | * | 3/1967 | De Luca ...................... | 604/272 |
| 4,785,868 A | * | 11/1988 | Koenig, Jr. ............. | 604/272 X |
| 4,932,961 A | * | 6/1990 | Wong et al. ................ | 606/223 |
| 5,002,564 A | * | 3/1991 | McGregor et al. ........... | 606/223 |
| 5,002,565 A | * | 3/1991 | McGregor .................. | 606/223 |
| 5,030,228 A | * | 7/1991 | Wong et al. ................ | 606/223 |
| 5,536,259 A | * | 7/1996 | Utterberg .................... | 604/272 |
| 5,575,780 A | * | 11/1996 | Saito ........................... | 604/272 |
| 5,683,416 A | * | 11/1997 | McGregor et al. .......... | 606/223 |
| 5,749,897 A | * | 5/1998 | Matsutani et al. .......... | 606/222 |
| 5,752,942 A | | 5/1998 | Doyle et al. | |
| 6,009,933 A | | 1/2000 | Doyle et al. | |

FOREIGN PATENT DOCUMENTS

| | | |
|---|---|---|
| JP | 6225940 A | 8/1994 |
| JP | 8187287 A | 7/1996 |
| JP | 9056819 A | 3/1997 |
| JP | 10328302 A | 12/1998 |

\* cited by examiner

*Primary Examiner*—John Rivell
(74) *Attorney, Agent, or Firm*—Young & Basile, P.C.

(57) ABSTRACT

A tip portion of a needle main body having an edge point includes a first slant surface slanted at 10–18 degrees with respect to the axis of the needle main body, a pair of second slant surfaces slanted at 16–23 degrees, and a pair of third slant surfaces slanted at 19–27 degrees. The ratios of the lengths of the first, second, and third slant surfaces are set to be 40–50%, 5–15%, and 35–55%. At the time of forming the second slant surfaces and the third slant surfaces, a grinding wheel or the needle main body is turned relative to the other in a horizontal plane so that the direction of axis of the grinding wheel and the direction of axis of the needle main body are in a twisted or distorted relationship from a substantially orthogonal relationship such that the radial outer sides of the second and the third slant surfaces are included downwardly.

4 Claims, 4 Drawing Sheets

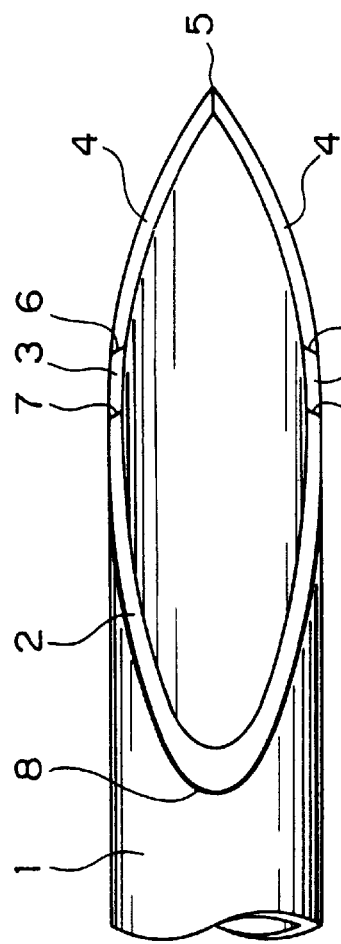
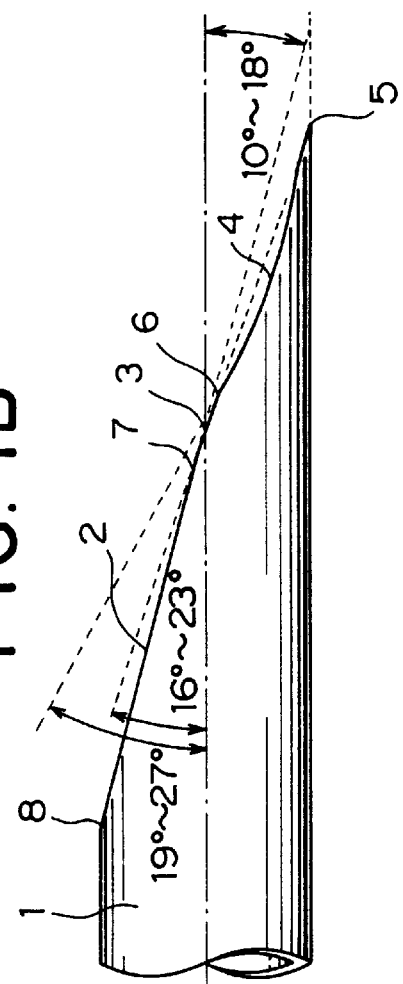
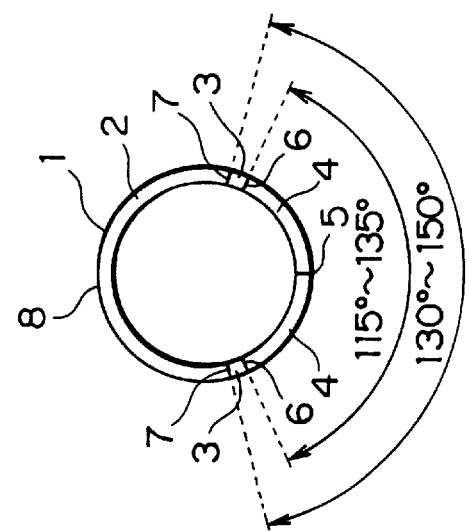

NEEDLE FOR INJECTION SYRINGE AND METHOD FOR MANUFACTURING THE SAME

BACKGROUND OF THE INVENTION

1. Field of the Invention

The present invention relates to a needle for injection syringe for medical use and a method for manufacturing the same, and in particular, suitable for a large needle for injection syringe having a diameter of 1.4 mm or larger used for artificial dialysis.

2. Description of the Related Art

Such a large needle as mentioned above generally causes a great pain at the time of sticking or penetrating as compared with a thin needle for hypodermic injection. In order to reduce the pain at the time of sticking or penetrating such a needle, for example, a needle as shown in FIG. 4 is employed. This needle for injection syringe has a shape of so-called lancet point, and a taper-shaped tip portion is formed by cutting a cylindrical needle main body 21 obliquely from one side thereof by grinding or the like. More specifically, this tip portion includes a first slant surface 22 contiguous to an outer peripheral surface of the cylindrical needle main body 21 and formed at a predetermined angle with respect to an axis of the needle main body 21, and a pair of second slant surfaces 24, 24 contiguous to the first slant surface 22 and contiguous to an edge point 25 and formed at a larger angle with respect to the axis of the needle main body 21 than that of the first slant surface 22. In this respect, the angle of the first slant surface 22 with respect to the axis of the needle main body 21 is about 10 degrees to 17 degrees, and similarly, the angle of the second slant surfaces 24, 24 with respect to the axis of the needle main body 21 is about 20 degrees to 25 degrees.

In forming these slant surfaces, first, the first slant surface 22 is ground by an outer peripheral surface of a column-shaped grinding wheel with a direction of rotation of the grinding wheel at a contact point with the needle main body 21 in parallel with or in coincident with the axis of the cylindrical needle main body 21. Then, the grinding wheel or the needle main body 21 is turned in a horizontal plane relative to the other so that an axis of the column-shaped grinding wheel and the axis of the cylindrical needle main body 21 are in a twisted relationship from a substantially orthogonal relationship. In other words, the direction of rotation of the grinding wheel at the contact point with the needle main body 21 and the direction of the axis of the needle main body 21 are deviated from each other. In this condition, the pair of slant surfaces 24, 24 are ground by the outer peripheral surface of the grinding wheel. As a result, the first slant surface 22 is parallel to a direction of a diameter of the needle main body 21 and is flat or substantially flat as a whole. The pair of slant surfaces 24, 24 are line symmetrical sandwiching the axis of the needle main body 21, and when viewed from the direction of the axis of the needle main body 21 so that the first slant surface 22 appears above the pair of slant surfaces 24, 24, both the pair of slant surfaces 24, 24 fall downwardly at radial outer sides thereof. Furthermore, axially middle portions of the pair of slant surfaces 24, 24 are recessed depending on a radius of the grinding wheel.

Due to a difference between slant angles of the slant surfaces, ridges 23, 23 (such ridges are referred to as ridges of the second slant surfaces 24, 24) are formed at contiguous portions of the first slant surface 22 and the the second slant surfaces 24, 24, however, as mentioned above, since both the second slant surfaces 24, 24 fall downwardly at radial outer sides thereof, the ridges 23, 23 of the second slant surfaces 24, 24 also fall downwardly at radial outer sides thereof. A relative turn angle between the grinding wheel and the needle main body 21 at the time of grinding the second pair of slant surfaces 24, 24 is set such that when viewed the cylindrical needle main body 21 from the direction of the axis of the needle main body 21, and angle between the ridges 23 and 23 around the outer periphery of the needle main body 21 is in a range from 110 degrees to 130 degrees. Such an angle is set so as to reduce the pain at the time of sticking of the needle.

In the needle for injection syringe as shown in FIG. 4, maximum values of resistance force at the time of sticking occur at three points including the edge point 25, the ridges 23, 23 (these portions are also referred to as junctions) of the second slant surfaces 24, 24, and a farthest portion (this portion is also referred to as a heel) 28 from the edge point 25 in a ridge of the first slant surface 22. As the number of the maximum values of resistance force increases, the pain increases and the cutting quality is deteriorated. Among theses maximum values, the maximum values of the resistance force at the edge point 25 and the heel 28 cannot be avoided, and also the maximum values of the resistance force at the ridges (or junctions) 23, 23 cannot be avoided at least as far as the lancet point type needle for injection syringe is concerned.

SUMMARY OF THE INVENTION

The present invention was developed to solve the problems mentioned above, and it is an object to provide a needle for injection syringe and a method of manufacturing the same, which eliminates the maximum values of resistance force at the ridges and which reduces the pain with an excellent cutting quality.

A needle for injection syringe according a first aspect of the invention includes a taper-shaped tip portion formed by cutting a tip portion of a cylindrical needle main body obliquely from one side thereof, and the taper-shaped tip portion of said needle comprises: a first slant surface contiguous to an outer peripheral surface of the cylindrical needle main body and formed at a predetermined angle with respect to an axis of the needle main body; a pair of second slant surfaces contiguous to the first slant surface and formed at a larger angle with respect to the axis of the cylindrical needle main body than the predetermined angle of the first slant surface; and a pair of third slant surfaces contiguous to the second slant surfaces and contiguous to an edge point and formed at a larger angle with respect to the axis of the cylindrical needle main body than the angle of the second slant surfaces.

In a needle for injection syringe according a second aspect of the invention, in the first aspect of the invention, the predetermined angle of the first slant surface with respect to the axis of the needle main body is in a range from 10 degrees to 18 degrees, and the angle of the second slant surfaces with respect to the axis of the needle main body is in a range from 16 degrees to 23 degrees, and the angle of the third slant surfaces with respect to the axis of the needle main body is in a range from 19 degrees to 27 degrees, and the angles are larger in the order of the first slant surface, the second slant surfaces, and the third slant surfaces.

In a needle for injection syringe according a third aspect of the invention, in the first aspect of the invention, a ratio of a length of the first slant surface along the axis of the needle main body to a whole length of the tip portion of the needle is 40% to 50%, a ratio of a length of the second slant surfaces to the whole length of the tip portion is 5% to 15%, and a ratio of a length of the third slant surfaces to the whole length of the tip portion is 35% to 50%.

A method of manufacturing a needle for injection syringe according a fourth aspect of the invention is a method of manufacturing the needle for injection syringe according to the first aspect of the invention, and the method comprises the steps of: grinding the first slant surface by the outer peripheral surface of the grinding wheel by aligning the direction of rotation of the column-shaped grinding wheel at the contact point of the grinding wheel with the cylindrical needle main body in parallel to or in coincident with the axis of the needle main body; grinding the pair of second slant surfaces by the outer peripheral surface of the grinding wheel by turning the grinding wheel or the needle main body relative to the other in a horizontal plane so that an axis of the column-shaped grinding wheel and the axis of the cylindrical needle main body are in a twisted relationship from a substantially orthogonal relationship thereby making the direction of rotation of the column-shaped grinding wheel at the contact point of the grinding wheel with the cylindrical needle main body deviated from the direction of the axis of the needle main body; and grinding the pair of third slant surfaces by the outer peripheral surface of the grinding wheel by turning the grinding wheel or the needle main body relative to the other in a horizontal plane so that the axis of the column-shaped grinding wheel and the axis of the cylindrical needle main body are in a twisted relationship from the substantially orthogonal relationship thereby making the direction of rotation of the column-shaped grinding wheel at the contact point of the grinding wheel with the cylindrical needle main body deviated from the direction of the axis of the needle main body.

In a method of manufacturing a needle for injection syringe according a fifth aspect of the invention, in the fourth aspect of the invention, the turn angle of the grinding wheel or the needle main body relative to the other at the time of grinding the second slant surfaces is selected such that, when viewed the cylindrical needle main body from the direction of axis thereof, an angle between the ridges of the second slant surfaces around the outer periphery of the needle main body is in a range from 130 degrees to 150 degrees, and the turn angle of the grinding wheel or the needle main body relative to the outer at the time of grinding the third slant surfaces is selected such that, when viewed the cylindrical needle main body from the direction of axis thereof, an angle between the ridges of the third slant surfaces around the outer periphery of the needle main body is in a range from 115 degrees to 135 degrees.

BRIEF DESCRIPTION OF THE DRAWINGS

FIGS. 1A, 1B and 1C show an embodiment of a needle for injection syringe and a method of manufacturing the same according to the present invention, in which FIG. 1A is a plan view, FIG. 1B is a front view, and FIG. 1C is a side view.

FIGS. 4A to 4C show an example of a prior art needle for injection syringe, in which FIG. 4A is a plan view, FIG. 4B is a front view, and FIG. 4C is a side view.

DESCRIPTION OF THE PREFERRED EMBODIMENTS

Figure 2A:
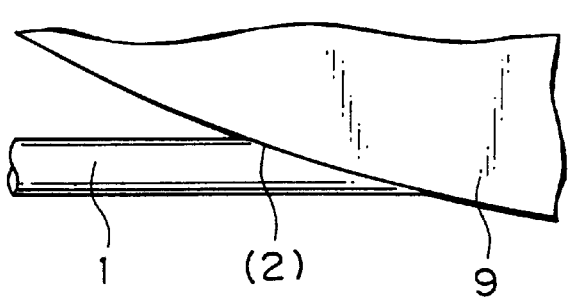
FIGS. 2A and 2F are diagrams for explaining the method of manufacturing the needle for injection syringe shown in FIGS. 1A to 1C.

Hereinafter, embodiments of a needle for injection syringe and its manufacturing method of the present invention will be explained. In the embodiments, the needle is a relatively large needle having a diameter of 1.4 mm to 2.1 mm and used, for example, for artificial dialysis.

FIGS. 1A to 1C show details of a tip portion of the needle for injection syringe of the embodiments. This tip portion is formed in a taper-shaped by cutting obliquely an end portion of a cylindrical needle main body from one side thereof. As is well known, since the needle for injection syringe is cylindrical, in order to form the tip portion, there is no other ways than to cut obliquely from one side of the needle main body.

This tip portion includes on the cut surface a first slant surface 2 contiguous to an outer periphery of the cylindrical needle main body 1 and formed at a predetermined angle with respect to an axis of the needle main body, a pair of second slant surfaces 3, 3 contiguous to the first slant surface 2 and formed at a larger angle with respect to the axis of the needle main body 1 than that of the first slant surface 2, and a pair of third slant surfaces 4, 4 contiguous to the second slant surfaces 3, 3 and contiguous to an edge point 5 and formed at a larger angle with respect to the axis of the needle main body 1 than that of the second slant surfaces 3, 3.

Among these angles, the angle of the first slant surface 2 with respect to the axis of the needle main body 1 is in a range from 10 degrees to 18 degrees, the angle of the second slant surfaces 3, 3 with respect to the axis of the needle main body 1 is in a range from 16 degrees to 23 degrees, and the angle of the third slant surfaces 4, 4 with respect to the axis of the needle main body 1 is in a range from 19 degrees to 27 degrees. The angle of each slant surface with respect to the axis of the needle main body 1 is set to reduce the resistance force at the time of sticking as small as possible, and for example, when the angle of the first slant surface 2 is less than 10 degrees, the length of an edge face becomes too long and it is not practical for sticking purpose, and when it is larger than 18 degrees, although the amount of sticking is small due to a shorter edge face length, the resistance of a heel portion at the time of penetrating becomes large. Furthermore, when the angle of the second slant surfaces 3, 3 is less than 16 degrees, and for example, when an angle difference from the first slant surface 2 exceeds 4 degrees, the resistance of the ridges 7, 7 at the time of passing becomes large. Also when the angle of the second slant surfaces 3, 3 is larger than 23 degrees, and for example, when an angle difference from the first slant surface 2 exceeds 4 degrees, the resistance of the ridges 6, 6 at the time of passing becomes large. Furthermore, when the angle of the third slant surfaces 4, 4 is less than 19 degrees, although the resistance of the ridges 6, 6 at the time of passing becomes small, the edge face length might become too long. Furthermore, when the angle of the third slant surfaces 4, 4 is larger than 27 degrees, and for example, when the angle difference from the second slant surfaces 3. 3 exceeds 4 degrees, the resistances of the ridges 6, 6 at the time of passing becomes large.

The ratios of the lengths in the axis direction of the needle main body 1 of the first slant surface 2, the second slant surfaces 3, 3, and the third slant surfaces 4, 4 are respectively set to 40%–50%, 5%–15%, and 35%–55%. The ratios of the respective slant surfaces are also set to reduce the resistance force at the time of sticking as small as possible. Here, the edge point 5 of the third slant surfaces 4, 4 is sticked into a blood vessel for the first time, and the cut opening is enlarged by each ridge formed by each slant surface at the outer peripheral portion of the needle. However, when the total ratio of the first slant surface 2 and the second slant surfaces 3, 3 is small, since the cut opening is not enlarged until the outer diameter of the main body 1 is reached, it is preferable to make the total ratio of the above-mentioned both slant surfaces fall in a range of 45%–50%.

Figure 2B:
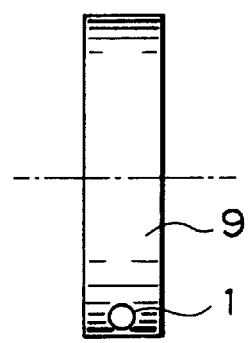
Figure 2C:
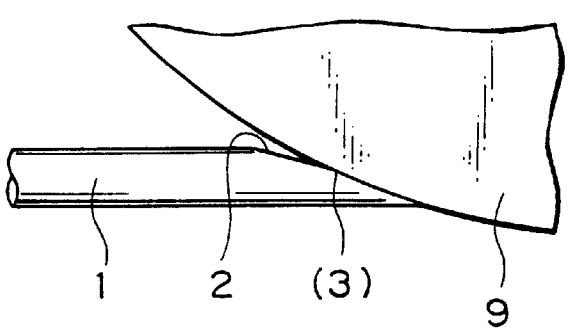
Figure 2D:
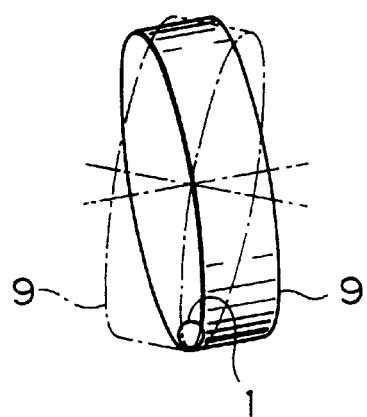
Figure 2E:
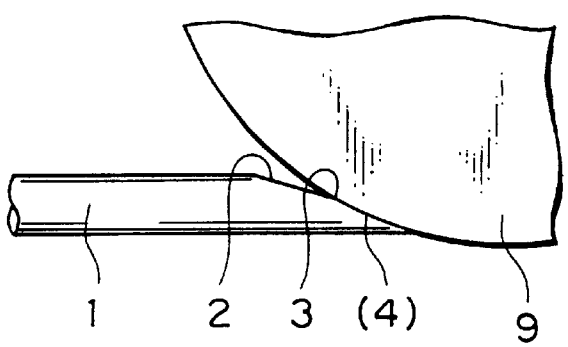
Figure 2F:
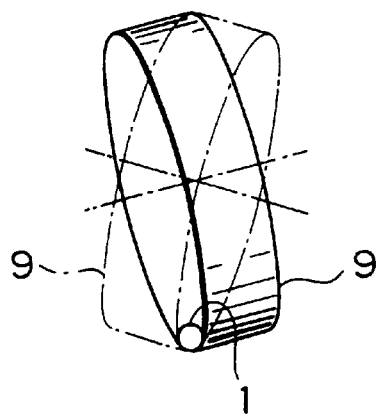

In order to form the tip portion of the needle main body 1, first, as shown in FIGS. 2A and 2B, the direction of rotation of a column-shaped grinding wheel 9 at the contact point with the needle main body 1 is made to coincide with or in parallel with the axis direction of the cylindrical needle main body 1, and the first slant surface 2 is ground by the outer peripheral surface of the grinding wheel 9. Next, as shown in FIGS. 2C and 2D, the grinding wheel 9 or the needle main body 1 is turned in a horizontal plane relative to the other so that the axis of the grinding wheel 9 and the axis of the cylindrical main body 1 are in a twisted or distorted relationship with each other from a substantially orthogonal relationship (for example, in FIG. 2D, the grinding wheel 9 is turned to a position shown by a solid line, actually, the needle main body 1 is turned). In this condition, that is, the direction of rotation of the grinding wheel 9 at the contact point with the needle main body 1 is made to deviate from the direction of axis of the cylindrical main body 1, either one of the second slant surfaces 3, 3 contiguous to the first slant surface 2 is ground by the outer peripheral surface of the grinding wheel 9, and subsequently, the grinding wheel 9 or the main body 1 is turned in the opposite direction relative to the other (for example, in FIG. 2D, the grinding wheel 9 is turned to a position shown by a long—and—short—dash line, actually, the main body 1 is turned) and in this condition, that is, the direction or rotation of the grinding wheel 9 at the contact point with the main body 1 is made to deviate from the direction of axis of the cylindrical main body 1, the rest of the second slant surfaces 3, 3 contiguous to the first slant surface 2 is ground. Next, as shown in FIGS. 2E and 2F, the grinding wheel 9 or the main body 1 is turned in a horizontal plane relative to the other so that the axis of the grinding wheel 9 and the axis of the cylindrical main body 1 are twisted or distorted with each other (for example, in FIG. 2F, the grinding wheel 9 is turned to a position shown by a solid line, actually, the main body 1 is turned). In this condition, that is, the direction of rotation of the grinding wheel 9 at the contact point with the main body 1 is made to deviate from the axis of the cylindrical main body 1, either one of the third slant surfaces 4, 4 contiguous to the second slant surface 3, 3 is ground by the outer peripheral surface of the grinding wheel 9, and subsequently, the grinding wheel 9 or the main body 1 is turned in the opposite direction relative to the other (for example, in FIG. 2F, the grinding wheel 9 is turned to a position shown by a long—and—short—dash line, actually, the main body 1 is turned). and in this condition, that is, the direction of rotation of the grinding wheel 9 at the contact point with the needle main body 1 is made to deviate from the direction of axis of the cylindrical main body 1, the rest of the third slant surfaces 4, 4 contiguous to the second slant surface 3, 3 is ground.

Accordingly, the first slant surface 2 is parallel to a direction of a laterally extending diameter of the cylindrical main body 1, and it is flat or substantially flat as a whole, however, the second slant surfaces 3, 3 are line symmetric sandwiching the axis of the needle main body 1, and when viewed from the direction of axis of the needle main body 1 so that the first slant surface 2 is viewed above, the radial outer sides of both the pair of slant surfaces 3 and 3 fall or incline downwardly, that is, the slant surfaces 3 and 3 are inclined outwardly and downwardly with respect to the axis of the needle main body 1. Similarly, the third slant surfaces 4, 4 are line symmetric sandwiching the axis of the needle main body 1, and when viewed from the direction of axis of the needle main body 1 so that the first slant surface 2 is viewed above, the radial outer sides of both the pair of slant surfaces 4 and 4 fall or incline downwardly, Furthermore, each of the slant surfaces 4 and 4 has a recessed potion at a center portion along the axis of the needle main body 1 depending on a radius of the grinding wheel 9. In this respect, although each of the second slant surfaces 3, 3 has a recessed portion just after the grinding work, most of the recessed portion is cut out depending on the ratio of the length of the second slant surfaces 3, 3 to that of the third slant surfaces 4 and 4.

Furthermore, the ridges 7 (hereinafter, referred to as the ridges of the second slant surfaces) formed at the connecting portions between the first slant surface 2 and the second slant surfaces 3, 3, and the ridges 6 (hereinafter, referred to as the ridges of the third slant surfaces) formed at the connecting portions between the second slant surface 3, 3 and the third slant surfaces 4, 4, which ridges are formed due to a difference between the slant angles of respective slant surfaces and due to a relative turn between the grinding wheel 9 and the needle main body 1, also fall downwardly at the radial outer sides thereof. This outward and downward inclination of the ridges is determined depending on the diameter of the grinding wheel 9 and the turn angle thereof, and this inclination determines the outward inclination of the second slant surfaces 3, 3 and the third slant surfaces 4, 4 whose radial outer sides are falling downwardly with respect to the axis of the needle main body 1. Here, the turn angle of the grinding wheel 9, in other words, the downward inclination angle of the radial outer sides of the second slant surfaces 3, 3 and the third slant surfaces 4, 4 is set so that when the cylindrical main body 1 is viewed from the axis direction of the main body 1, the angle (also referred to as an outer peripheral angle) between the ridges 7 and 7 around the outer periphery of the main body 1 is made to be 130 degrees to 150 degrees, and similarly, the angle between the ridges 6 and 6 around the outer periphery of the main body 1 is made to be 115 degrees to 135 degrees. These outer peripheral angles of these slant surfaces are set so as to make the resistance force at the time of sticking as small as possible. In particular, when the outer peripheral angle of the third slant surfaces 4, 4 between the ridges 6 and 6 is set to be 115 degrees to 135 degrees, the edge at the boundary between the slant surfaces 4, 4 and the outer peripheral surface of the main body 1 becomes sharp with respect to the blood vessel, and the cutting performance is excellent. However, when it exceeds 135 degrees, the tip, end of the tip point 5 becomes wide and the resistance force at the time of sticking increases. In selecting the outer peripheral angles between the ridges 6 and 6, and between the ridges 7 and 7, it is the premise that the outer peripheral angles between the ridges 7 and 7 is larger than that between the ridges 6 and 6.

In this needle for injection syringe, as shown in FIG. 1B, there are four discontinuous points including the tip point 5, the heel 8, the ridges (junctions) 7, 7 of the second slant surfaces, and the ridges (junctions) 6, 6 of the third slant surfaces. The sticking, penetration tests were conducted by using this needle, and changes in the resistance force were measured. The test conditions are as follows.

Sticking and Penetration Test

Object Material for Sticking and Penetration (Sticking and Penetration Material): polyethylene sheet having a thickness t=0.05 mm Needle Speed: 40 mm/min Room Temperature: 22.5° C.

Silicone Coating (needle material)

Figure 3A:
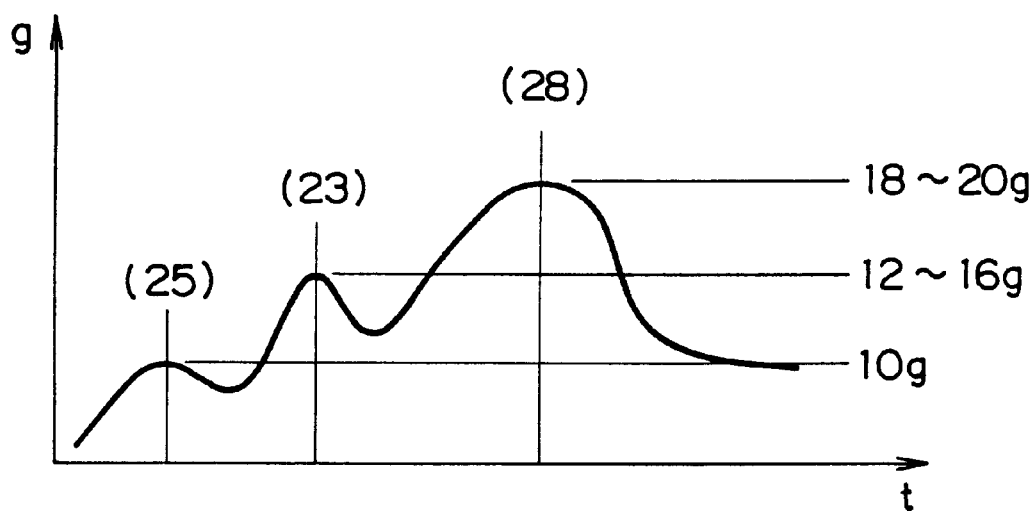
FIGS. 3A and 3B are graphs for explaining the results of sticking tests of a prior art needle and the needle for injection syringe shown in FIGS. 1A to 1C.
Figure 3B:
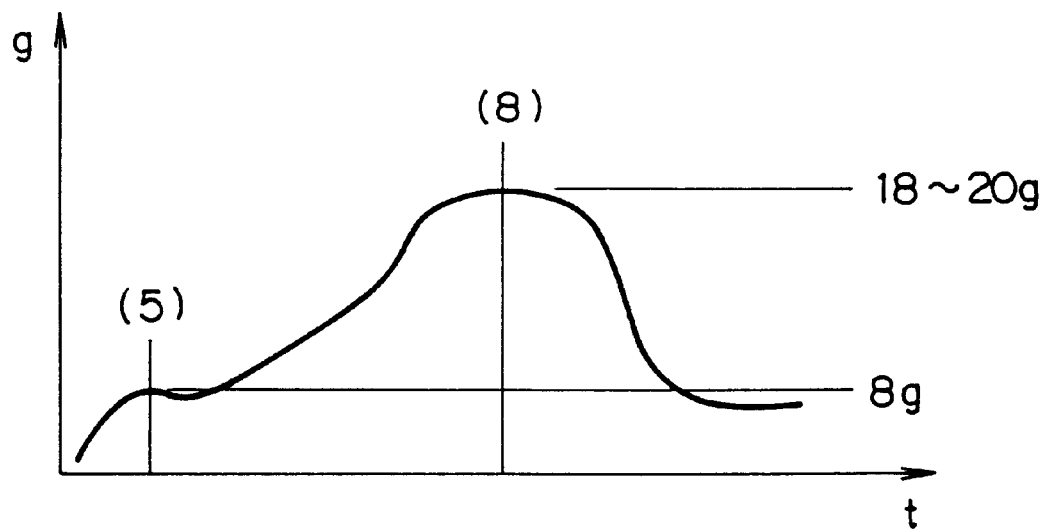
Figure 4A:
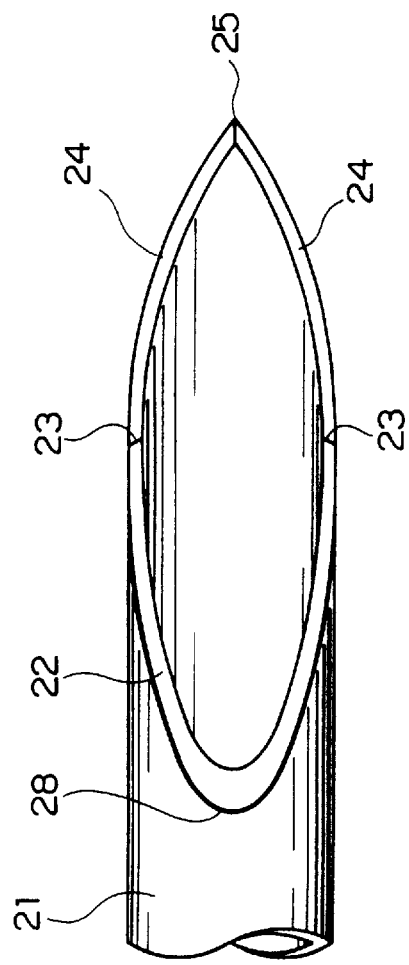
Figure 4B:
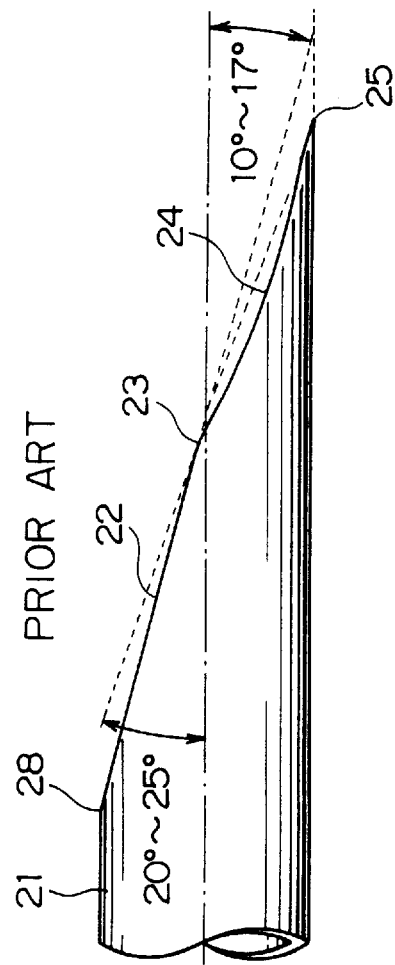
Figure 4C:
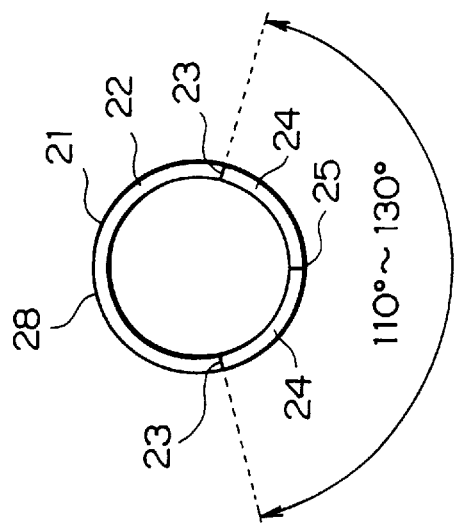

The test results are shown by a graph in FIG. 3B. On the other hand, the results of sticking test of a conventional lancet type needle for injection syringe are shown by a graph in FIG. 3A. As will be seen from FIG. 3A, in the conventional lancet type needle, the maximum values of the resistance force (g) appear at three points including the edge point (25), the ridges (23), and the heel (28), whereas in the needle for injection syringe in the present embodiment, the maximum values of the resistance force (g) appear only at two points including at the edge point (5) and the heel (8), and the maximum values of the resistance force do not appear at the ridges 7 and ridges 6. As a result, the needle for injection syringe in the present embodiment is excellent in the cutting performance and the pain is also reduced by the amount corresponding to the lack of the maximum values at the ridges.

As mentioned above, since the abrupt angle difference or change between the first and the second and the third slant surfaces makes the resistance force at the ridges become large, it is possible to improve the cutting performance by providing a moderate or slow angle difference.

Furthermore, the length of the tip point is set to a suitable length depending on the use in medical practice, and in the case where the length of the tip point becomes short, a priority has been given to the length even when the resistance of the ridges is increased. However, since the pain is increased when the length of an edge face formed by the surface of the taper-shaped tip portion is increased, it is preferable to form the slant surfaces into three stages in order to reduce the length of the edge face.

As described in the foregoing, the needle for injection syringe and the method for manufacturing the same according the present invention provide the advantage that the number of the maximum values of the resistance force at the time of sticking can be reduced, and the cutting performance is excellent and the pain is also reduced.

What is claimed is:

1. A needle for an injection syringe having a taper-shaped tip portion formed by cutting a tip portion of a cylindrical needle main body obliquely from one side thereof, the taper-shaped tip portion of said needle comprising:

a first slant surface contiguous to an outer peripheral surface of the cylindrical needle main body and formed at a predetermined angle with respect to an axis of the needle main body;

a pair of second slant surfaces contiguous to the first slant surface and symmetric with respect to the axis of the needle main body and formed at a larger angle with respect to this axis of the needle main body than the predetermined angle of the first slant surface; and a pair of third slant surfaces contiguous to the second slant surfaces and symmetric with respect to the axis of the needle main body and contiguous to an edge point, said pair of third slant surfaces being formed at a larger angle with respect to the axis of the needle main body than the angle of the second slant surfaces, wherein an inclination angle of the ridges formed at the connecting portions between the first slant surface and the second slant surface is in a range from 130 degrees to 150 degrees when the cylindrical main body is viewed from the axis direction of the main body, and a inclination angle of the ridges formed at the connecting portions between the second slant surface and the third slant surface is in a range from 115 degrees to 135 degrees when the cylindrical main body is viewed from the axis direction of the main body.

2. A needle for injection syringe according to claim 1, wherein said predetermined angle of the first slant surface with respect to the axis of the needle main body is in a range from 10 degrees to 18 degrees, and the angle of the pair of second slant surfaces with respect to the axis of the needle main body is in range from 16 degrees to 23 degrees, and the angle of the pair of third slant surfaces with respect to the axis of the needle main body is in a range from 19 degrees to 27 degrees, and the angle increase in the order of the first slant surfaces, the second slant surfaces, and the third slant surfaces.

3. A needle for injection syringe according to claim 1, wherein a ratio of a length of the first slant surface along the axis of the needle main body to a whole length of the tip portion is 40% to 50%, a ratio of a length of the pair of second slant surfaces to the whole length of the tip portion is 5% to 15% and a ratio of a length of the pair of third slant surfaces to the whole length of the tip portion is 35% to 50%.

4. A method for manufacturing a needle for injection syringe which is defined in claim 1, said method comprising the steps of:

grinding the first slant surface of the needle main body by an outer peripheral surface of a grinding wheel by aligning the needle so that a part of the direction of rotation of a column-shaped grinding wheel is in parallel to or in coincident with the axis of the needle main body;

grinding the second slant surfaces of the needle main body by the outer peripheral surface of the grinding wheel by turning one of the grinding wheel and the needle main body relative to the other in a horizontal plane so that the axis of the column-shaped grinding wheel and the axis of the cylindrical needle main body are in a twisted relationship from a substantially orthogonal relationship thereby making the direction of rotation of the column-shaped grinding wheel at the contact point of the grinding with the cylindrical needle main body deviate from the direction of the axis of the needle main body; and grinding the third slant surfaces by the outer peripheral surface of the grinding wheel by turning one of the grinding wheel and the needle main body relative to the other in a horizontal plane so that the axis of the column-shaped grinding wheel and the axis of the cylindrical needle main body are in a twisted relationship from the substantially orthogonal relationship thereby making the direction of rotation of the column-shaped grinding wheel at the contact point of the grinding wheel with the cylindrical needle main body deviate from the direction of the axis of the needle main body, wherein an angle of turn of one of the grinding wheel and the needle main body relative to the other at the time of grinding the second slant surfaces is set such that, when viewed the cylindrical needle main body from the direction of axis thereof, an angle between the ridges of the second slant surfaces around the outer periphery of the needle main body is in the range from 130 degrees to 150 degrees, and an angle of turn of one of the grinding wheel and the needle main body relative to the other at the time of grinding the third slant surfaces is set such that, when viewed the cylindrical needle main body from the direction of axis thereof, an angle between the ridges of the third slant surfaces around the outer periphery of the needle main body is in a range from 115 degrees to 135 degrees.

* * * * *